United States Patent

Diaz et al.

[11] Patent Number: 5,795,576
[45] Date of Patent: Aug. 18, 1998

[54] CHEMICAL COMPOSITION FOR AIDING THE ABSORPTION, BINDING AND ELIMINATION OF UNDIGESTED FAT

[76] Inventors: Jose A. Diaz, 2950 Jackson Ave., Coconut Grove, Fla. 33133; Eduardo M. Naranjo, 14021 Cypress Ct., Miami Lakes, Fla. 33014

[21] Appl. No.: 888,848

[22] Filed: Jul. 7, 1997

Related U.S. Application Data

[60] Provisional application No. 60/022,375 Jul. 8, 1996.
[51] Int. Cl.$^6$ .................... A61K 35/78; A61K 31/715; A61K 31/70
[52] U.S. Cl. ..................... 424/195.1; 514/54; 514/62
[58] Field of Search ............... 514/62, 54; 424/195.1

[56] References Cited

U.S. PATENT DOCUMENTS

| | | | |
|---|---|---|---|
| 4,758,861 | 7/1988 | Gori | 426/74 |
| 5,104,676 | 4/1992 | Mahmoud et al. | 426/590 |
| 5,462,742 | 10/1995 | Bogentoft et al. | 424/439 |
| 5,612,039 | 3/1997 | Policappelli et al. | 424/195.1 |
| 5,690,981 | 11/1997 | Watanabe et al. | 426/531 |

*Primary Examiner*—Raymond Henley, III
*Attorney, Agent, or Firm*—Malloy & Malloy, P.A.

[57] ABSTRACT

A moisture activated composition is provided for ingestion by humans to aid in absorbing and binding undigested fat for rapid elimination from the human body. This composition, in a preferred embodiment comprises a fibrous agent, such as psyllium, in an amount of generally about 80% by weight of the composition, an amount of glucosamine HCL generally about 10% by weight of the composition, and amounts of glucomannan, apple pectin, and stearic acid forming the other generally about 10% by weight of the composition.

11 Claims, No Drawings

CHEMICAL COMPOSITION FOR AIDING THE ABSORPTION, BINDING AND ELIMINATION OF UNDIGESTED FAT

BACKGROUND OF THE INVENTION

1. Claim of Priority

The present application is based on and a claim to priority under 35 U.S.C. Section 119(e) is made to a provisional patent application filed with the U.S. Patent Office on Jul. 8, 1996 and assigned Ser. No. 60/021,299.

2. Field of the Invention

The present invention relates to a chemical composition for ingestion by humans for aiding weight loss and more particularly, to a chemical composition which when ingested by a human prior to eating a meal, aids in the absorption and binding of undigested fat to a fibrous agent for rapid elimination from the human body.

3. Description of the Related Art

In this day and age, many people's lifestyles have become less physically active. A natural result of a sedentary lifestyle is the tendency to gain weight. Indeed, it is commonly thought that many people are now over-weight with obesity being a growing problem. Due to this trend, countless efforts have been made to help people control their weight. As a few examples, many have proclaimed to have won the "battle of the bulge" with a specific diet program or a particular exercise program. Others have explored hypnosis and other mechanisms for controlling the appetite of an individual. Others in the scientific arena have formulated sugar substitutes and are pursuing fat substitutes as methods to reduce the caloric intake of an individual without hopefully, sacrificing the taste of otherwise highly fattening foods. While these efforts are generally capable of aiding many in their fight to lose weight or to maintain a desired weight, many are in general, ineffective or simply not practical. For example, some good meaning souls have tried in earnest to follow a particular diet plan but eventually, fall off the plan lacking will-power to continue for weeks and months at a time. This is equally true of those who try hypnosis and similar weight-loss gimmicks. Finally, some view sugar substitutes as being tasteless or worse, as carrying an intolerable health risk, given that some studies have linked them to carcinogens and/or the formation of brain tumors.

It has been appreciated in recent years that the fat content of foods eaten are a major culprit behind human weight gain. For example, regardless of the type of fat present in a food product, fat has the highest caloric value per gram—about 9 large calories per gram—of any food group. It is understood that the body tends to store fat for future use, rather than to utilize its immediately, and this factor helps lead to weight-gain. Unfortunately, fat also makes many food items more tasty—whether butter on bread, dressings on salads, sour cream on potatoes, or frosting on cake—and are therefore, difficult to eliminate entirely from one's diet. Thus, fat usually finds its way into the body. Once it does so, a healthy body automatically secretes lipase, an enzyme that accelerates synthesis of fats, i.e., breaking down the fat molecule. The majority of all fats in foods are present in "triglyceride form", which the body seeks to break down by removing the glycerol molecule from the triglyceride and thereby, release the free fatty acids. Once this occurs, the body is well on its way to absorbing the fat and likely, storing same instead of utilizing it for energy.

From the foregoing, it will be understood that there remains an appreciable need in the art for a product which facilitates a person's efforts to lose weight and/or to control his or her weight and yet which is safe and easy to implement. There remains a need in the art for a product and method which aids a person in losing weight or in maintaining a stable weight, which does not rely exclusively on will power. Any such product or method should not interfere with the taste of foods. Ideally, any such product or method would permit the a person to eat the foods that they most like, regardless of fats contained therein, and would prevent the body from absorbing the fat in such foods once they have been eaten and further, would aid the body in rapid elimination of the absorbed fats in a safe and comfortable manner. The present invention is designed to satisfy the needs in the art and is believed to represent a significant advance in the field of weight loss.

SUMMARY OF THE INVENTION

The present invention provides a novel, chemical composition for ingestion by humans which aids in weight loss or in maintaining a stable weight. In particular, when the chemical composition of the present invention is ingested by a human prior to eating a meal, the composition acts to absorb and bind undigested fat to a fibrous agent so as to promote its rapid elimination from the human body. In accordance with this invention, the novel composition is moisture activated such that it remains inert and can be formed into capsules, preferably conveniently sized for ingestion by a human, and will remain inert until it comes into contact with bodily secretions whether water or other liquid. The composition consists of a mixture of an amount of psyllium generally about 83% by weight, an amount of glucosamine HCL generally about 8% by weight, an amount of glucomannan generally about 6% by weight, an amount of apple pectin generally about 2% by weight and an amount of stearic acid generally about 1% by weight of the composition. Upon contact with moisture, the composition begins to break down and becomes activated. Once activated, the composition acts quickly, usually within 30 seconds to seek and attach itself to undigested fats such as oils and the like, and typically, within about 2 minutes will form a small mass of undigestible fibrous material. Additionally, a method for using the chemical composition is also described which comprises the steps of forming a capsule of generally about 500 milligrams containing the chemical composition and having a human ingest at least one of said capsules with generally about eight ounces of water generally about fifteen minutes or generally about twenty minutes before a meal.

A primary object of the present invention is to provide a convenient and effective means for aiding weight loss in a human which safely affects only the fat portion of foods ingested by the human without affecting metabolism.

Another primary object of the present invention is to provide a chemical composition which seeks out, attaches and binds undigested fat ingested by a human to a fibrous agent, forming an undigestible mass which can easily and rapidly be eliminated from the human's body.

A feature of the chemical composition according to the present invention is that moisture activated and therefore, is inert and can be formed into and stored as conveniently sized capsules until being ingested by a human and activated by coming into contact with bodily secretions whether water or other liquid.

Yet another object of the present invention is to provide a chemical composition which includes a blend of fibrous material for aiding the human body in rapid elimination of waste.

A feature of the present invention in the form of one 500 milligram capsule is that it can absorb up to twelve times its own weight or generally about 3 to 6 grams of undigested fats.

These and other objects, features and advantages of the present invention will become readily apparent from the detailed description, which follows.

DETAILED DESCRIPTION OF THE PREFERRED EMBODIMENT

The present invention is directed towards a chemical composition for ingestion by humans which acts to absorb and bind undigested fat and rapidly eliminating the undigested fat from the human body. The present invention is also directed to a method of aiding weight loss in humans.

The chemical composition of the present invention primarily comprises at least one fibrous agent to act both as a vehicle for absorbing fat and as a medium for allowing a human to feel full. In the preferred embodiment, the fibrous agent used is psyllium and comprises generally between 80% and 90% by weight of the composition. In the most preferred embodiment, psyllium comprises generally about 85% and ideally, 83% by weight of the composition. In the preferred embodiment, the composition of the present invention may additionally comprise one or more other fibrous agents. For example, plantago ovata seed mucilage or the cover or husks of psyllium seeds may be utilized, which are very fibrous materials. Other fibrous agents may also be utilized, as described more fully below.

In addition to a fibrous agent, the composition of the present invention comprises glucosamine, a material derived from deacetylated shellfish shells or chitin. Chitin is known in the art as a naturally occurring polysaccharide—a polymer or long molecules consisting of sugar molecules strung together as shown by the general formula:

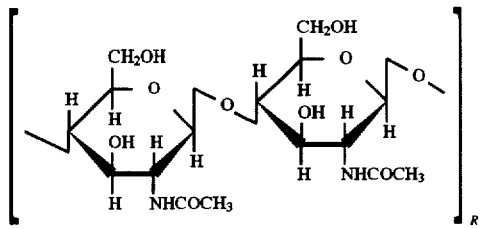

Chitin, which can be obtained from crab, lobster or shrimp shells by dissolving the shells' calcium carbonate and then removing protein fragments, leaving behind chitin as a white powder, normally cycles through the environment, decomposing naturally into its hydrogen, carbon, nitrogen and oxygen building blocks. In one embodiment of the invention, glucosamine may be obtained from chitin by hydrolysis. Preferably, glucosamine salts and compounds derived from a monomer of chitin, namely, N-acetyl-D-glucosamine (GlcN Ac) which is represented by the general formula:

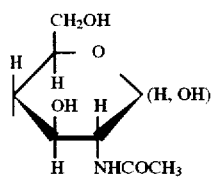

will be utilized such as, for example, glucosamine hydrochloride, acetylated glucosamines, and/or D-glucosamine. In a most preferred embodiment, glucosamine HCL and/or glucosamine hydrochloride will be utilized and will comprise generally about 10% and ideally 8% by weight of the composition. Glucosamine hydrochloride offers an additional side benefit in that it has been shown to be an efficacious alternative to corticosteroid treatment of enteritis and colonitis. It will be understood by those of ordinary skill in the art that as a derivative of chitosan, which has an ability to chelate various metal ions because of its hydroxy and amino groups act as electron donors, glucosamine HCL is an ion, or molecule having a negative charge, and which therefore, attracts and binds with certain molecules of food. In an alternative embodiment, a beta-alkylglycoside of N-acetyl-D-glucosamine may be utilized, which is represented by the general formula:

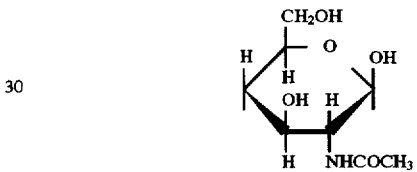

and is believed to effectively increase the ability of one's digestive tract to handle substantial quantities of lactose. In yet another alternative embodiment, the composition may comprise chitosan, instead of glucosamine. Chitosan is formed by dunking the chitin, in its white powder form, in a concentrated sodium hydroxide solution heated to above 135 degrees Celsius to remove one of chitin's side groups, i.e., to hydrolize the N-acetyl linkage, such that chitosan results, which can be more readily dissolved. Chitosan, which is represented by the general formula:

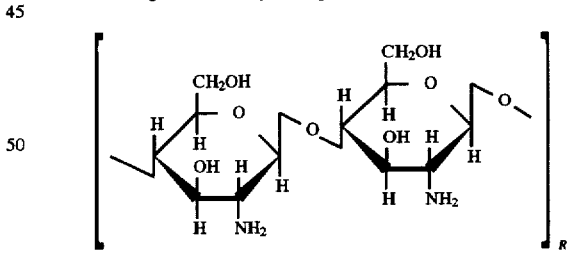

also has the ability to act as a coagulant, i.e., to attract and bind with certain molecules such as amino acids and proteins.

In the preferred embodiment of the present invention, the chemical composition comprises, in addition to psyllium and glucosamine HCL, a quantity of glucomannan—also known as Konjak or Konjac Root—which serves the purpose of providing lubrication and as well as providing an additional fibrous agent to the composition. Ideally, glucomannan comprises generally about 5% and ideally 6% by weight of the composition. In addition, the chemical composition further comprises a pectin obtained from fruits or succulent vegetables which serves the purpose of providing an additional fibrous agent to the composition. Most preferably, an apple pectin is used to form the composition which ideally, comprises generally about 2% by weight of the composition. Finally, in the preferred embodiment, the chemical composition also comprises a saturated fatty acid such as stearic acid, which serves the purpose of permitting the capsule containing the composition to be smooth. Ideally, stearic acid comprises generally about 1% by weight of the composition.

In the preferred embodiment, the psyllium, glucosamine HCL, glucomannan, apple pectin and stearic acid are mixed together in powder form, although a granular form might also be suitable, and result in a mixture which is inert until it comes into contact with water, or another liquid such as is produced by the human body during digestion. Thus, in a most preferred embodiment, the present invention can be formed into capsules for being easily packaged and stored. Additionally, the material used to form the encasement of the capsule will be inert and upon coming into contact with water or other liquid, will begin to break down and permit both the release and activation of the chemical composition. If desired, the capsules containing the chemical composition according to the present invention may be packaged into bottles containing 50, 60, 75, 80, 100 or more capsules, and may include a small, separately wrapped quantity of a drying agent, such as a silica gel in order to aid dry conditions for preserving the composition inert until use by a human.

Ideally, the present invention will be formed into capsules containing generally about 500 milligrams of the chemical composition in the following amounts: generally about 83% by weight of psyllium; generally about 8% by weight of glucosamine HCL; generally about 6% by weight of glucomannan; generally about 2% by weight of apple pectin; and generally about 1% by weight of stearic acid. It will be appreciated that a capsule containing about 500 milligrams has a size and overall dimension which is readily suited for being comfortably swallowed by a person, although the capsule could be formed to be contain less or more of the chemical composition (with ratios of the composition similar to that disclosed herein), and thereby be somewhat larger or smaller, and still function for being ingested by a person. Testing experiments with the above described chemical composition have demonstrated the ability to absorb up to 12 times its own weight or about 3 to 6 grams of undigested fats. For instance, in one experiment 70 milliliters of water was placed in an appropriately sized test tube along with 2 grams of wheat germ oil and 100 milligrams of lecithin. This mixture was shaken vigorously for about 10 seconds. Next, 1000 milligrams of the chemical composition according to the present invention (two capsules of 500 mg each) were added and again, the mixture was shaken vigorously for about 10 seconds. After several minutes, the mixture was observed as having approximately ninety-five (95%) percent of fat (oil layer) gone, i.e., fat was no longer visible but instead had become bound with the fibrous agent of the composition so as to form an undigestible mass.

In addition, the chemical composition of the present invention lends itself to a method of aiding human weight loss, which will now be described. In particular, the chemical composition of the present invention seeks out and binds with fat ingested by a human prior to its being absorbed into the body, and as has been explained, binds them to a fibrous agent so as to aid the person in feeling "full" and further, to permit rapid elimination by the human body. The method of the present invention comprises the steps of forming a capsule of generally about 500 milligrams with the chemical composition and having the human ingest at least one of the 500 milligram capsules with generally about eight ounces of water generally about fifteen to twenty minutes before a meal. Ideally, the human will ingest two of the capsules before a meal, but may ingest up to about four of the capsules (2000 milligrams) if the meal to be eaten is especially large and/or has a particularly high fat content. Upon being ingested by a human, each capsule begins to disintegrate and releases or otherwise facilitates activation of the chemical composition contained therein in typically, generally about thirty (30) minutes, and often less time. In a preferred form of the method there is an additional step of having the human ingest generally about eight ounces of water upon waking up in the morning, and ideally, there is an additional step of having the human ingest generally about eight ounces of water between meals.

Since many modifications, variations and changes in detail can be made to the described preferred embodiment of the invention, it is intended that all matters in the foregoing description be interpreted as illustrative and not in a limiting sense. Thus, the scope of the invention should be determined by the appended claims and their legal equivalents.

Now that the invention has been described,

What is claimed is:

1. A chemical composition for ingestion by a human at meal-times, which aids in absorbing and binding undigested fat for rapid elimination from the human's body, said composition comprising:

a) an amount of a fibrous agent generally about 83% by weight of said composition;

b) an amount of glucosamine HCL generally about 8% by weight of said composition;

c) an amount of glucomannan generally about 6% by weight of said composition;

d) an amount of apple pectin generally about 2% by weight of said composition; and e) an amount of stearic acid generally about 1% by weight of said composition.

2. A chemical composition as recited in claim 1, wherein said fibrous agent comprises psyllium.

3. A chemical composition as recited in claim 1, wherein said composition is formed into a capsule of 500 milligrams.

4. A chemical composition for ingestion by a human at meal-times, which aids in absorbing and binding undigested fat for rapid elimination from the human's body, said composition containing:

a) an amount of a fibrous agent generally about 80% by weight of said composition;

b) an amount of glucosamine HCL generally about 8 to ten percent (8%–10%) by weight of said composition;

c) an amount of glucomannan generally about 5% by weight of said composition;

d) an amount of apple pectin generally about 2% by weight of said composition; and e) an amount of stearic acid generally about 2% by weight of said composition.

5. A chemical composition as recited in claim 4, wherein said fibrous agent comprises psyllium.

6. A method of absorbing and binding undigested fat ingested by a human and for rapidly eliminating same from the human, said method comprising the steps of:

a) forming a capsule of generally about 500 milligrams with a chemical composition comprising:

i) an amount of psyllium generally about 83% by weight of said composition;

ii) an amount of glucosamine HCL generally about 8% by weight of said composition;

iii) an amount of glucomannan generally about 6% by weight of said composition;

iv) an amount of apple pectin generally about 2% by weight of said composition; and v) an amount of stearic acid generally about 1% by weight of said composition; and b) having the human ingest at least one of said capsules with generally about eight ounces of water generally about fifteen minutes before a meal.

7. A method as recited in claim 6, wherein the human ingests two of said capsules.

8. A method as recited in claim 6, wherein the human ingests three of said capsules.

9. A method as recited in claim 6, wherein the human ingests four of said capsules.

10. A method as recited in claim 6, further comprising the step of having the human ingest generally about eight ounces of water upon waking up in the morning.

11. A method as recited in claim 6, further comprising the step of having the human ingest generally about eight ounces of water between meals.

\* \* \* \* \*

UNITED STATES PATENT AND TRADEMARK OFFICE
CERTIFICATE OF CORRECTION

PATENT NO.   : 5,795,576                                              Page 1 of 1
DATED        : August 8, 1998
INVENTOR(S)  : Jose A. Diaz and Eduardo M. Naranjo It is certified that error appears in the above-identified patent and that said Letters Patent is hereby corrected as shown below:

<u>Title page,</u>
Item [60], Related U.S. Application Data, after "Provisional application No." should read -- 60/021,299 --

Signed and Sealed this

Twenty-fifth Day of November, 2003

JAMES E. ROGAN
*Director of the United States Patent and Trademark Office*